(12) United States Patent
Dorian et al.

(10) Patent No.: US 11,759,795 B2
(45) Date of Patent: Sep. 19, 2023

(54) BLOOD WASHING AND SEPARATION SYSTEM

(71) Applicants: Randel E. Dorian, San Diego, CA (US); Zimmer, Inc., Warsaw, IN (US)

(72) Inventors: Randel E. Dorian, San Diego, CA (US); Matthew D. Landrigan, Fort Wayne, IN (US); Kyle Kausch, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 880 days.

(21) Appl. No.: 16/609,689

(22) PCT Filed: May 18, 2018

(86) PCT No.: PCT/US2018/033432
§ 371 (c)(1),
(2) Date: Oct. 30, 2019

(87) PCT Pub. No.: WO2018/213728
PCT Pub. Date: Nov. 22, 2018

(65) Prior Publication Data
US 2020/0197956 A1   Jun. 25, 2020

Related U.S. Application Data

(60) Provisional application No. 62/508,820, filed on May 19, 2017.

(51) Int. Cl.
*B04B 5/04* (2006.01)
*A61M 1/36* (2006.01)
(Continued)

(52) U.S. Cl.
CPC ......... *B04B 5/0442* (2013.01); *A61M 1/3693* (2013.01); *A61M 1/3692* (2014.02);
(Continued)

(58) Field of Classification Search
CPC ..... B04B 5/0442; B04B 11/04; B04B 11/082; B04B 2005/045; B04B 15/12; A61M 1/3693; A61M 1/3692; B01D 2221/10
(Continued)

(56) References Cited

U.S. PATENT DOCUMENTS

| 7,866,485 B2 * | 1/2011 | Dorian | A61M 1/3482 494/67 |
| 2009/0250413 A1 * | 10/2009 | Hoeppner | B01D 21/262 210/513 |
| 2009/0289014 A1 * | 11/2009 | Hoeppner | A61M 1/3693 210/90 |

FOREIGN PATENT DOCUMENTS

| EP | 0987037 A2 * | 3/2000 | .......... A61M 1/3698 |
| WO | WO-2018213728 A1 | 11/2018 | |

OTHER PUBLICATIONS

"International Application Serial No. PCT US2018 033432, International Preliminary Report on Patentability dated Nov. 28, 2019", 9 pages.

(Continued)

*Primary Examiner* — Walter D. Griffin
*Assistant Examiner* — Shuyi S. Liu
(74) *Attorney, Agent, or Firm* — SCHWEGMAN LUNDBERG & WOESSNER, P.A.

(57) ABSTRACT

A blood washing system (20) having a rotor (22) defining an internal chamber for receiving a multi-component fluid and a skimmer assembly (24) including a moveable buoy (28) having an orifice (32) fluidly connected to an access port for the rotor for selectively withdrawing separated fractions of the multi-component fluid. The multi-component fluid can be fed into the internal chamber before the rotor (22) can be rotated at a first speed to fractionate the multi-component fluid. A brake can be applied to the rotor to slow rotation of the rotor to a slower second speed or stop rotation of the (Continued)

rotor causing the solid and denser fluid fractions to settle on the bottom wall (44) of the rotor (22). The buoy (28) can have a specific gravity corresponding to a selected fraction such that the buoy floats on a surface of the selected fraction, wherein the fractions floating on the selected fraction can be withdrawn through the orifice (32).

19 Claims, 2 Drawing Sheets

(51) Int. Cl.
    *B04B 11/04*     (2006.01)
    *B04B 11/08*     (2006.01)

(52) U.S. Cl.
    CPC ........... *B01D 2221/10* (2013.01); *B04B 11/04* (2013.01); *B04B 11/082* (2013.01); *B04B 2005/045* (2013.01)

(58) Field of Classification Search
    USPC ........................................ 210/90, 741; 494/1
    See application file for complete search history.

(56) References Cited

OTHER PUBLICATIONS

"International Application Serial No. PCT/US2018/033432, International Search Report dated Aug. 10, 2018", 5 pgs.
"International Application Serial No. PCT/US2018/033432, Written Opinion dated Aug. 10, 2018", 7 pgs.

* cited by examiner

BLOOD WASHING AND SEPARATION SYSTEM

CLAIM OF PRIORITY

This application is a U.S. National Stage Application under 35 U.S.C. 371 from International Application Serial No. PCT/US2018/033432 filed on May 18, 2018, and published as WO 2018/213728 A1 on Nov. 22, 2018 which claims the benefit of U.S. Provisional Patent Application Ser. No. 62/508,820, filed on May 19, 2017, the benefit of priority of each of which is claimed hereby, and each of which is incorporated by reference herein in its entirety.

TECHNICAL FIELD

This document pertains generally, but not by way of limitation, to separation systems and related methods for separating of components of a multiple component material.

BACKGROUND

Whole blood samples are often fractionated to separate red blood cells, platelets, and other cellular materials from the plasma and other fluid components of the whole blood. A selected fraction, typically red blood cells or cellular materials, can be selectively withdrawn from the fractionated whole blood sample for use in certain medical applications. The isolated cellular material is often further processed by adding one or more wash fluids to the isolated cellular materials to remove any plasma or other undesirable fluids or materials clinging to or intermixed with the desired cellular material. The resulting wash solution comprising cellular material within the wash fluids is often fractionated again to separate and isolate the cellular material from the wash fluids.

For certain medical applications, the cellular materials must often be washed multiple times to cleanse the cellular material to certain predetermined standards. However, each wash cycle requires the addition of new wash fluids, fractionation of the wash solution, and isolation of the cellular materials from the wash fluids, which is time-consuming and is often labor intensive. Also, as the wash solution is typically centrifuged to fractionate the wash solution, separate containers must be connected to add or withdraw wash solution from the centrifuge rotor before being disconnected to permit rotation of the centrifuge rotor for fractionation. The repeated connection and disconnection of separate containers can increase the risk of contamination or degradation of cellular material within the centrifuge rotor.

OVERVIEW

The present inventors have recognized, among other things, that a problem to be solved can include efficiently washing cellular material without excessive risk of contamination or degradation of the cellular material. In an example, the present subject matter can provide a solution to this problem, such as by providing a rotor defining an internal chamber for receiving a multi-component fluid and a skimmer assembly including a moveable buoy. The moveable buoy can have an orifice fluidly connected to an access port for the rotor for selectively withdrawing separated fractions of the multi-component fluid. The multi-component fluid can be fed into the internal chamber before the rotor can be rotated at a first speed to fractionate the multi-component fluid. A brake can be applied to the rotor to slow rotation of the rotor to a slower second speed or stop rotation of the rotor, which can cause the solid fractions and denser fluid fractions to settle on the bottom wall of the rotor.

The buoy can have a specific gravity corresponding to a selected fraction such that the buoy floats on a surface of the selected fraction, wherein the orifice is oriented such that the fractions floating on the selected fraction can be withdrawn through the orifice. Additional fluids (e.g. wash fluids, diluents) can be added to the isolated fractions within the internal chamber through the orifice of the buoy prior to rotation of the rotor at the first speed for fractionation. The contaminated wash fluids can be fractionated from the mixture and withdrawn such that the "washed" selected fraction remains. After the targeted fractions have been sufficiently washed, the selected fraction can be entrained within a wash fluid or other fluid before being withdrawn from the internal chamber through the orifice of the buoy.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components.

The drawings illustrate generally, by way of example, but not by way of limitation, various embodiments discussed in the present document.

DETAILED DESCRIPTION

Figure 1:
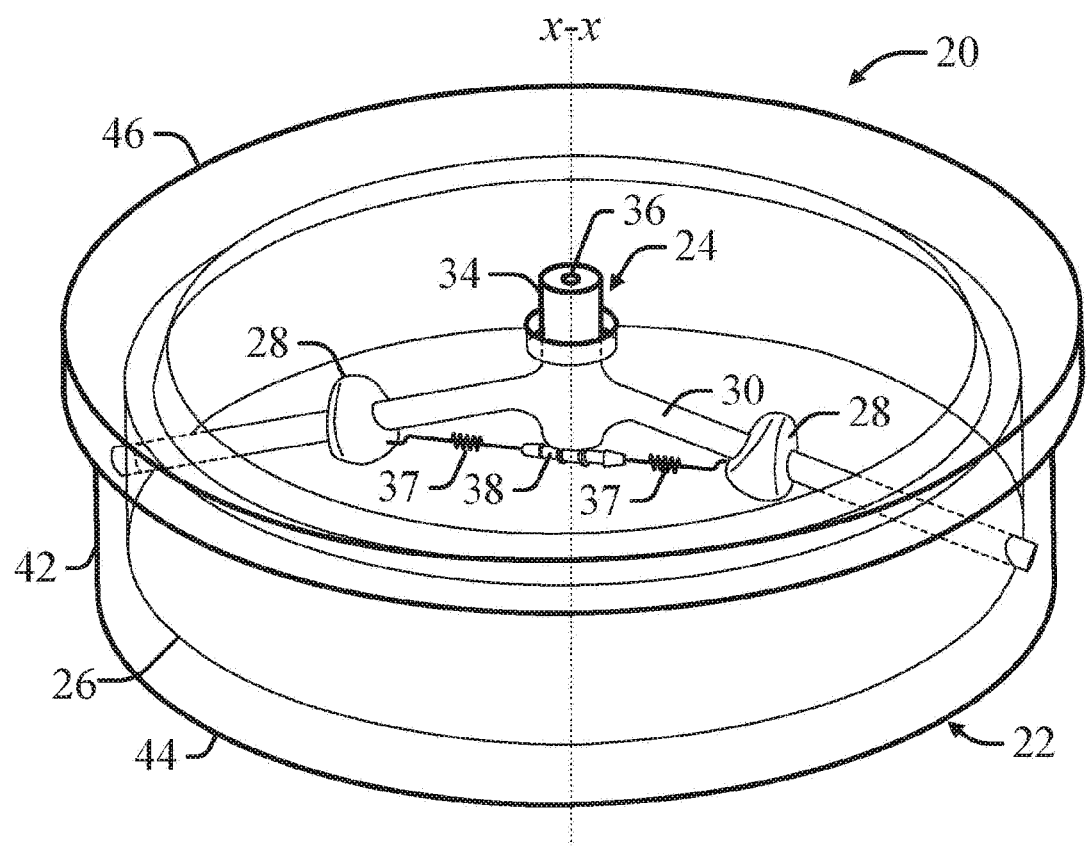
FIG. 1 is a schematic, partial cross-sectional top perspective view of the blood washing system according to an example of the present disclosure.

As depicted in FIG. 1, a blood washing system 20 for washing cellular material, according to an example, can include a rotor 22 for fractionating a multi-component fluid and a skimmer assembly 24 for withdrawing a selected fraction of the multi-component fluid from the rotor 22. The rotor 22 can define an internal chamber 26 for receiving a multi-component fluid, such as a whole blood sample, a wash solution comprising cellular material suspended in a wash fluid, or other multi-component fluids containing solid material suspended in a fluid. The rotor 22 can be rotated about a rotational axis x-x to fractionate the multi-component fluid into a plurality of fractions. The plurality of fractions can comprise at least one solid fraction containing the solid material (e.g. red blood cells) and at least one liquid fraction containing the liquid material (e.g. plasma). In certain examples, the plurality of fractions can comprise multiple liquid fractions each having a different density. The skimmer assembly 24 can include a buoy 28 moveable along a buoy track 30 within the internal chamber 26. The buoy 28 can float on a surface of a selected fraction or a boundary between adjacent fractions. The buoy 28 can define an orifice 32 (shown in FIGS. 2-3) through which material, such as an unwanted fraction (e.g. plasma), can be withdrawn from the internal chamber 26 to isolate the selected fraction (e.g. red blood cells).

Figure 2:
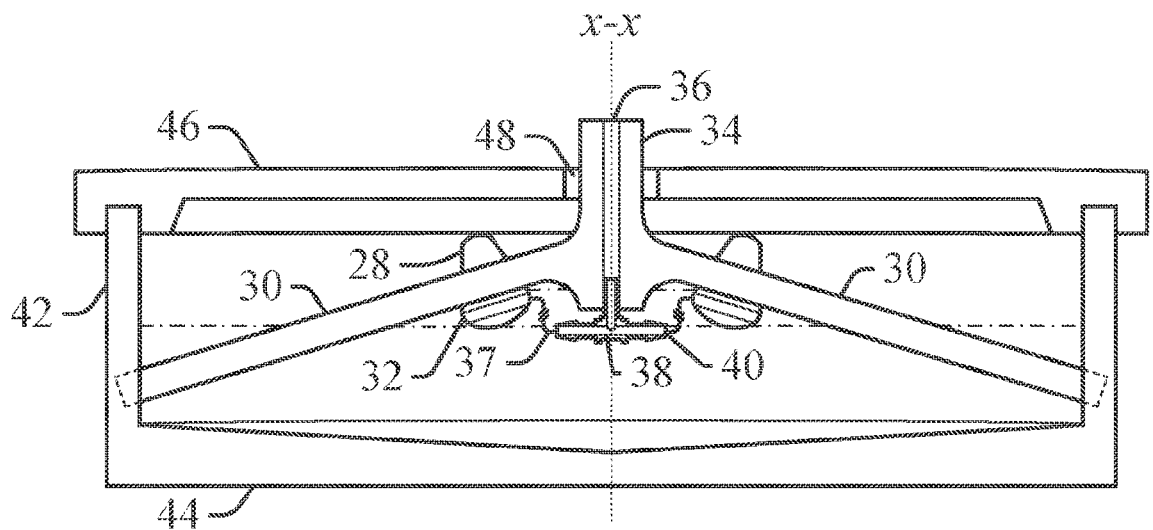
FIG. 2 is a cross-sectional side view of a blood washing system having floats floating on a surface of a supernatant according to an example of the present disclosure.
Figure 3:
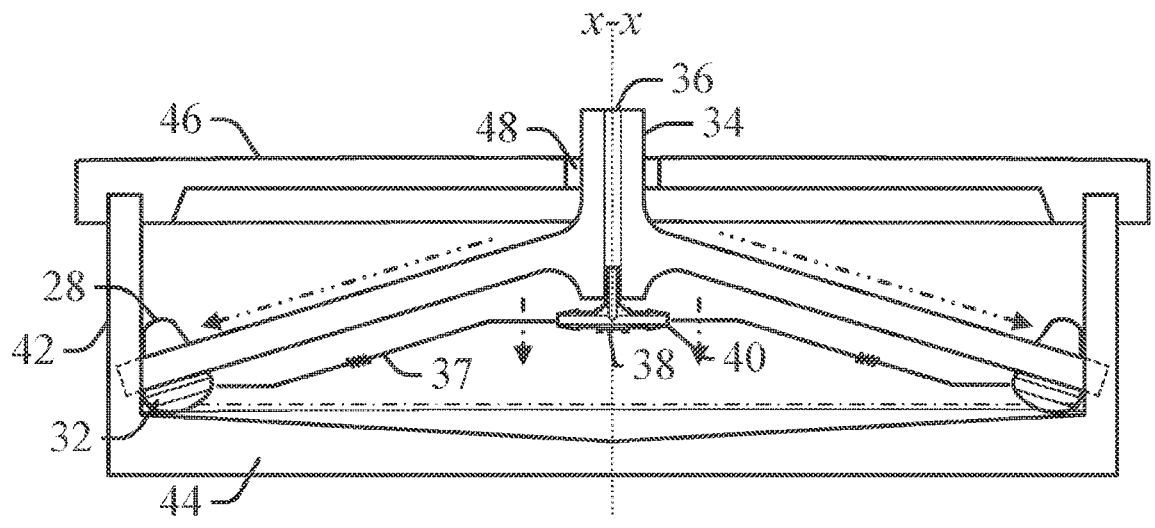
FIG. 3 is a cross-sectional side view of the blood washing system depicted in FIG. 2, wherein the floats move to track the surface of the supernatant as the supernatant is withdrawn.

As depicted in FIGS. 1-3, in an example, the skimmer assembly 24 can include an access tube 34 that extends through the rotor 22 into the internal chamber 26. The access tube 34 can define an access channel 36 through which material can be withdrawn from or fed into the internal chamber 26. In an example, the access tube 34 can be oriented such that the access tube 34 is centered on the rotational axis x-x such that the access channel 36 is centered on the rotational axis x-x. The access channel 36 can be fluidly connected to the orifice 32 of the buoy 28 by an adjustable connector or tube 37. The adjustable tube 37 can comprise a coil tube or other connector configured to adjustably maintain the fluid connection between the orifice 32 of the buoy 28 and the access channel 36 of the access tube 34 as the buoy 28 moves along the buoy track 30 within the internal chamber 26.

In an example, the skimmer assembly 24 can include a plurality of buoys 28, each buoy 28 being moveable along a buoy track 30. In this configuration, the skimmer assembly 24 can include an adapter 38 having a plurality of connectors 40, wherein an adjustable tube 37 can connect each connector 40 with an orifice 32 of a corresponding buoy 28 as illustrated in FIGS. 2 and 3. The connected buoys 28 can cooperate to withdraw the selected fraction through their respective orifices 32 and feed the material into the access channel 36. In an example, each buoy track 30 can extend radially outward from the rotational axis x-x such that the buoys 28 move radially inward and outward from the rotational axis x-x. The buoy tracks 30 are oriented evenly around the radial axis x-x to balance the rotor 22 as the rotor 22 is rotated.

As depicted in FIGS. 1-3, in an example, the rotor 22 can include a radial wall 42 extending from a bottom wall 44. The rotor 22 can include a top wall (not shown) integral to the radial wall 42 such that the radial wall 42 extends from the bottom wall 44 to the top wall to define the internal chamber 26. Alternatively, the rotor 22 can include a top cap 46 engagable to the radial wall 42 to such that the top cap 46 and the radial wall 42 and the bottom wall 44 cooperate to enclose the internal chamber 26. In certain examples, the access tube 34 can extend through an access port 47 defined by the top cap 46, wherein the rotor 22 can include a rotating seal 48 positioned in the access port 47 to permit rotation of the rotor 22 about the access tube 34.

As depicted in FIGS. 1-3, in an example, each buoy track 30 can be oriented radially outward and downward from the access tube 34. In this configuration, the buoy 28 moves radially and downward from the access tube 34 to rest on the surface of the selected fraction. As such, the lower volume of the selected fraction and/or underlying fractions, the further outward and lower the buoy 28 is positioned. The positioning of the buoy 28 can improve the stability of the rotor 22 during rotation.

In operation, a multi-component fluid can be received within the internal chamber 26 of the rotor, where the rotor 22 can be rotated about the rotational axis x-x at a first speed to fractionate the multi-component fluid within the internal chamber 26. In operation, the rotor 22 can be rotated about the rotational axis x-x at a first speed to fractionate the multi-component fluid within the internal chamber 26. The denser fluid and solid fractions are pushed further outward radially from the rotational axis x-x by the rotation of the rotor 22 while the less dense fluid fractions remain closer to the rotational axis x-x. The plurality of fractions can comprise at least one solid fraction containing the solid material and at least one liquid fraction containing the liquid material. In certain examples, the plurality of fractions can comprise multiple liquid fractions having different densities.

A brake can be applied to the rotor 22 to stop rotation of the rotor 22 or slow rotation of the rotor 22 to a second speed slower than the first speed causing the denser fluids and solids to settle toward the bottom wall 44. Lighter fluids of the fractionated components settle above the denser fractionated components. The buoy 28 can comprise a material or materials that provide the buoy 28 with a specific gravity that corresponds to a supernatant comprising the denser fractionated components. In an example, the specific gravity can be less than 1 g/cc. The buoy 28 can float of the surface of the supernatant or between the supernatant and a fraction floating on the supernatant. As illustrated in FIGS. 2 and 3, the orifice 32 can be positioned on the buoy 28 such that a lighter fraction or waste fluid settled on the supernatant can be withdrawn through the orifice 32 of the buoy 28 floating on the supernatant.

In an example, red blood cell compatible fluids can be supplied to solid fraction within the internal chamber 26 through the access tube 34 and the orifice 32 of the buoys 28. The RBC compatible fluids can include, but are not limited to solutions for rejuvenating RBCs within the solid fraction. For example, REJUVESOL red blood cell processing solution produced by BIOMET BIOLOGICS of Warsaw, Ind. can be added to the solid fraction. In this configuration, the rotor 22 can be rotated about rotational axis x-x at a low agitation speed to intermix or suspend the solid fraction with the RBC compatible fluids. In an example, the rotor 22 can be heated to about ordinary body temperature (37 C) during the agitation period to further improve rejuvenation of the RBCs. The agitation period can be about 60 minutes.

Wash fluids can be supplied to the internal chamber 26 through the access tube 34 and the orifice 32 of the buoys 28. The rotor 22 can be continuously rotated or pulsed about the rotational axis x-x to suspend or intermix at least the solid fraction with the additional wash fluids. The rotor 22 can then be rotated at the first speed or other high speed to fractionate the wash fluid-solid fraction mixture. Following fractionation, the brake can be applied to the rotor 22 to stop or slow rotation of the rotor 22 to the second speed or other slow speed to cause the heavier fractions to settle within the internal chamber 26 with the lighter fractions and/or wash fluids settling on the supernatant of the heavier fractions. The buoy 28 can re-settle on the surface of the supernatant such that the lighter fractions and/or wash fluids can be withdrawn through the orifice 32 of the buoy 28. The process can be repeated until the solid fraction is sufficiently washed. In an example, the wash fluids can be added after the red blood cell compatible fluids are added and the agitation period is completed.

The solid fraction can be withdrawn from the internal chamber 26 through the buoy 28 following washing of the solid fraction. To facilitate withdrawal of the solid fraction, additional wash fluid or diluent can be fed into the internal chamber 26. The rotor 22 can be rotated or pulsed to intermix the solid fraction with the wash fluid or diluent to suspend the solid fraction within the fluid. In an example, the rotor 22 can be rotated at a third speed slower than the first speed for breaking up the solid fraction and entraining the solid fraction within the fluid. The third speed can be determined to maintain the solid fraction within the wash fluid without fractionating the intermixed solid fraction within the additional fluid. The solid fraction entrained within the fluid can then be withdrawn from the internal chamber 26 through the orifice 32 of the buoy 28.

VARIOUS NOTES & EXAMPLES

Example 1 is a blood washing system, comprising: a rotor defining an internal chamber for receiving a multi-component fluid, the rotor being rotatable about a rotational axis at a first speed to fractionate the multi-component fluid into a plurality of fractions; and a skimmer assembly including at least one buoy moveable along a buoy track positioned within the internal chamber, wherein the buoy defines an orifice fluidly connected to an access port in the rotor; wherein the buoy comprises a specific gravity corresponding to a selected fraction of the plurality of fractions such that the buoy floats on the selected fraction.

In Example 2, the subject matter of Example 1 optionally includes the rotor having a radial wall extending from a bottom wall.

In Example 3, the subject matter of Example 2 optionally includes wherein the rotor further comprises: a top cap engagable to the radial wall to enclose the internal chamber; wherein the top cap defines the access port.

In Example 4, the subject matter of any one or more of Examples 1-3 optionally include wherein the skimmer assembly further comprises: an access tube extending through the access port, the access tube defining an access channel for moving materials into and out of the internal chamber; wherein the orifice of the buoy is fluidly connected to the access channel.

In Example 5, the subject matter of Example 4 optionally includes wherein access tube is configured to be coupled to a device for supplying or withdrawing fluid from the internal chamber of the rotor.

In Example 6, the subject matter of any one or more of Examples 4-5 optionally include wherein the access tube is aligned with the rotational axis.

In Example 7, the subject matter of any one or more of Examples 4-6 optionally include wherein the rotor further comprises: a rotating seal positioned within the access port to prevent passage of material around the access tube.

In Example 8, the subject matter of any one or more of Examples 4-7 optionally include wherein the buoy track extends radially outward from the access tube such that the buoy moves radially outward from the rotational axis along the buoy track.

In Example 9, the subject matter of Example 8 optionally includes wherein the buoy track is oriented downward such that the buoy moves downward as the buoy moves radially outward from the rotational axis along the buoy track.

In Example 10, the subject matter of any one or more of Examples 4-9 optionally include wherein the skimmer assembly comprises: a first buoy defining a first orifice and moveable on a first buoy track; and a second buoy defining a second orifice and moveable on a second buoy track; wherein the first buoy track and the second buoy track extend radially outward from the rotational axis in opposite directions to balance the rotor during rotation.

In Example 11, the subject matter of Example 10 optionally includes wherein the skimmer assembly further comprises: an adapter having a plurality of connectors including: a first connector connected to the first orifice, and a second connector connected to the second orifice; wherein the adapter is fluidly connected to the access channel to connect the first and second buoys to the access tube.

In Example 12, the subject matter of any one or more of Examples 1-11 optionally include wherein the bottom wall of the rotor includes a slanted surface slanted toward an apex.

In Example 13, the subject matter of any one or more of Examples 1-12 optionally include that the specific gravity of the buoy is less than 1 g/cc.

Example 14 is a method of washing blood, comprising: providing a multi-component fluid into an internal chamber of a rotor, wherein a skimmer assembly including at least one buoy moveable along a buoy track is positioned within the internal chamber; rotating the rotor at a first speed to fractionate the multi-component fluid into a plurality of fractions; braking the rotor to reduce the rotation of the rotor to a second speed slower than the first speed such that the plurality of fractions is stacked vertically within the rotor; wherein the buoy comprises a specific gravity corresponding to a selected fraction of the plurality of fractions such that the buoy floats on the selected fraction.

In Example 15, the subject matter of Example 14 optionally includes wherein the buoy defines an orifice fluidly connected to an access port in the rotor.

In Example 16, the subject matter of Example 15 optionally includes withdrawing at least one fraction of the plurality of the fractions floating above the selected fraction through the orifice in the buoy.

In Example 17, the subject matter of any one or more of Examples 14-16 optionally include wherein the selected fraction comprises a supernatant over a solid fraction.

In Example 18, the subject matter of Example 17 optionally includes adding wash fluids to the internal chamber; and rotating the rotor to agitate the solid fraction and intermix the wash fluids with the solid fraction.

In Example 19, the subject matter of Example 18 optionally includes rotating the rotor to fractionate the wash fluid and solid fraction into a plurality of fractions; braking the rotor to reduce the rotation of the rotor to stack the plurality of fractions vertically arranged within the rotor; and withdrawing at least one fraction of the plurality of the fractions floating above the supernatant of the selected fraction through the orifice in the buoy.

In Example 20, the subject matter of any one or more of Examples 17-19 optionally include adding a suspension quantity of wash fluids; rotating the rotor to agitate the solid fraction and intermix the wash fluids with the solid fraction; and withdrawing the intermixed solid and wash fluid mixture.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A blood washing system, comprising:
   a rotor defining an internal chamber for receiving a multi-component fluid, the rotor being rotatable about a rotational axis at a first speed to fractionate the multi-component fluid into a plurality of fractions;
   a skimmer assembly including at least one buoy moveable along a buoy track positioned within the internal chamber, wherein the buoy defines an orifice fluidly connected to an access port in the rotor; and
   a brake operable to reduce rotation of the rotor to a second speed slower than the first speed to stack the plurality of fractions vertically within the rotor;
   wherein the buoy track extends radially outward from the access port such that the buoy moves radially outward from the rotational axis along the buoy track;
   wherein the buoy track is oriented downward such that the buoy moves downward as the buoy moves radially outward from the rotational axis along the buoy track; and
   wherein the buoy comprises a specific gravity corresponding to a selected fraction of the plurality of fractions such that the buoy floats on the selected fraction.

2. The blood washing system of claim 1, the rotor having a radial wall extending from a bottom wall.

3. The blood washing system of claim 2, wherein the rotor further comprises:
   a top cap engageable to the radial wall to enclose the internal chamber;
   wherein the top cap defines the access port.

4. The blood washing system of claim 1, wherein the skimmer assembly further comprises:
   an access tube extending through the access port, the access tube defining an access channel for moving materials into and out of the internal chamber;
   wherein the orifice of the buoy is fluidly connected to the access channel.

5. The blood washing system of claim 4, wherein the access tube is configured to be coupled to a device for supplying or withdrawing fluid from the internal chamber of the rotor.

6. The blood washing system of claim 4, wherein the access tube is aligned with the rotational axis.

7. The blood washing system of claim 4, wherein the rotor further comprises:
   a rotating seal positioned within the access port to prevent passage of material around the access tube.

8. A blood washing system, comprising:
   a rotor defining an internal chamber for receiving a multi-component fluid, the rotor being rotatable about a rotational axis at a first speed to fractionate the multi-component fluid into a plurality of fractions; and
   a skimmer assembly including at least one buoy moveable along a buoy track positioned within the internal chamber, wherein the buoy defines an orifice fluidly connected to an access port in the rotor, the skimmer assembly further including an access tube extending through the access port, the access tube defining an access channel for moving materials into and out of the internal chamber;
   wherein the orifice of the buoy is fluidly connected to the access channel;
   wherein the buoy comprises a specific gravity corresponding to a selected fraction of the plurality of fractions such that the buoy floats on the selected fraction;
   wherein the buoy track extends radially outward from the access tube such that the buoy moves radially outward from the rotational axis along the buoy track; and
   wherein the buoy track is oriented downward such that the buoy moves downward as the buoy moves radially outward from the rotational axis along the buoy track.

9. The blood washing system of claim 4, wherein the skimmer assembly comprises:
   a first buoy defining a first orifice and moveable on a first buoy track; and
   a second buoy defining a second orifice and moveable on a second buoy track;
   wherein the first buoy track and the second buoy track extend radially outward from the rotational axis in opposite directions to balance the rotor during rotation.

10. The blood washing system of claim 9, wherein the skimmer assembly further comprises:
    an adapter having a plurality of connectors including:
    a first connector connected to the first orifice, and
    a second connector connected to the second orifice;
    wherein the adapter is fluidly connected to the access channel to connect the first and second buoys to the access tube.

11. The blood washing system of claim 2, wherein the bottom wall of the rotor includes a slanted surface slanted toward an apex.

12. The blood washing system of claim 1, wherein the specific gravity of the buoy is less than 1 g/cc.

13. A method of washing blood, comprising:
providing a multi-component fluid into an internal chamber of a rotor, wherein a skimmer assembly including at least one buoy moveable along a buoy track is positioned within the internal chamber;
rotating the rotor at a first speed to fractionate the multi-component fluid into a plurality of fractions;
braking the rotor to reduce the rotation of the rotor to a second speed slower than the first speed such that the plurality of fractions is stacked vertically within the rotor;
wherein the buoy comprises a specific gravity corresponding to a selected fraction of the plurality of fractions such that the buoy floats on the selected fraction.

14. The method of claim 13, wherein the buoy defines an orifice fluidly connected to an access port in the rotor.

15. The method of claim 14, further comprising:
withdrawing at least one fraction of the plurality of the fractions floating above the selected fraction through the orifice in the buoy.

16. The method of claim 13, wherein the selected fraction comprises a supernatant over a solid fraction.

17. The method of claim 16, further comprising:
adding at least one of wash fluids and red cell compatible fluids to the internal chamber; and
rotating the rotor to agitate the solid fraction and intermix the wash fluids with the solid fraction.

18. The method of claim 17, further comprising:
rotating the rotor to fractionate the wash fluid and solid fraction into a plurality of fractions;
braking the rotor to reduce the rotation of the rotor to stack the plurality of fractions vertically arranged within the rotor; and
withdrawing at least one fraction of the plurality of the fractions floating above the supernatant of the selected fraction through the orifice in the buoy.

19. The method of claim 16, further comprising:
adding a suspension quantity of wash fluids;
rotating the rotor to agitate the solid fraction and intermix the wash fluids with the solid fraction; and
withdrawing the intermixed solid and wash fluid mixture.

* * * * *